United States Patent
Salcedo et al.

(10) Patent No.: US 8,808,000 B2
(45) Date of Patent: Aug. 19, 2014

(54) GUIDED DENTAL IMPLANTATION SYSTEM AND ASSOCIATED DEVICE AND METHOD

(75) Inventors: Juan Ricardo Salcedo, Coral Gables, FL (US); Federico Grande, Stuart, FL (US)

(73) Assignee: Neocis, Inc., Miami, FL (US)

(*) Notice: Subject to any disclaimer, the term of this patent is extended or adjusted under 35 U.S.C. 154(b) by 381 days.

(21) Appl. No.: 12/416,710

(22) Filed: Apr. 1, 2009

(65) Prior Publication Data

US 2009/0253095 A1    Oct. 8, 2009

Related U.S. Application Data

(60) Provisional application No. 61/041,722, filed on Apr. 2, 2008.

(51) Int. Cl.
*A61C 1/00* (2006.01)
*A61C 3/00* (2006.01)
*A61C 8/00* (2006.01)

(52) U.S. Cl.
USPC ............... 433/75; 433/196; 433/215; 433/72

(58) Field of Classification Search
USPC ......... 433/75, 98, 108, 114, 213, 215, 72–74, 433/196; 606/130; 600/424
See application file for complete search history.

(56) References Cited

U.S. PATENT DOCUMENTS

| | | | |
|---|---|---|---|
| 5,343,391 A * | 8/1994 | Mushabac | 433/76 |
| 5,607,303 A | 3/1997 | Nakamura | |
| 6,296,483 B1 | 10/2001 | Champleboux | |
| 6,322,567 B1 | 11/2001 | Mittelstadt et al. | |
| 6,419,484 B1 | 7/2002 | DaSilva et al. | |
| 6,488,638 B2 * | 12/2002 | Mushabac | 600/590 |
| 6,640,128 B2 | 10/2003 | Vilsmeier et al. | |
| 7,014,461 B2 | 3/2006 | Weinstein | |
| 2002/0077542 A1 * | 6/2002 | Vilsmeier et al. | 600/424 |
| 2002/0160337 A1 * | 10/2002 | Klein et al. | 433/213 |
| 2004/0146830 A1 | 7/2004 | Weinstein | |
| 2004/0157188 A1 * | 8/2004 | Luth et al. | 433/75 |
| 2005/0186533 A1 * | 8/2005 | Cohen | 433/98 |
| 2006/0127848 A1 * | 6/2006 | Sogo et al. | 433/173 |
| 2006/0281991 A1 | 12/2006 | Fitzpatrick et al. | |

OTHER PUBLICATIONS

Hein, A.; Lueth, T.C.; Hommel, G., "Contact observation of interactive surgical robotics systems," Intelligent Robots and Systems, 1999. IROS '99. Proceedings. 1999 IEEE/RSJ International Conference on , vol. 2, No., pp. 733,739 vol. 2, 1999.*

(Continued)

*Primary Examiner* — Todd Manahan
*Assistant Examiner* — Michael R Ballinger
(74) *Attorney, Agent, or Firm* — Womble Carlyle Sandridge & Rice, LLP

(57) ABSTRACT

A dental implantation system is provided, comprising an implantation device adapted to prepare a site within a mouth of a patient for receiving a dental implant. A guidance device is operably engaged with the implantation device and is adapted to operably engage the mouth of the patient. The engagement between the guidance device and the mouth of the patient provides a fiducial marker for guiding the implantation device to prepare the site for receiving the dental implant. An associated method of implanting a dental implant, and associated devices, are also provided.

15 Claims, 5 Drawing Sheets

(56) References Cited

OTHER PUBLICATIONS

Figure 1A:
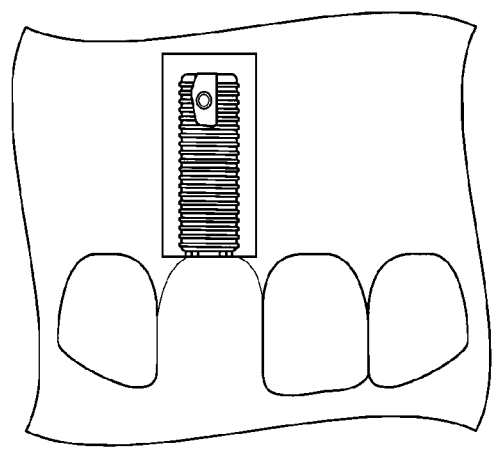

Brief, J., et al., "Computer-guided insertion of dental implants—a clinical evaluation," *International Congress Series*, 2001, vol. 1230, pp. 739-747.

Casap, N., et al., "Image-Guided Navigation System for Placing Dental Implants," *Compendium*, 2004, vol. 25(1), pp. 783-792.

Kramer, F., et al., "Navigated vs. conventional implant insertion for maxillary single tooth replacement," *Clin. Oral Impl. Res.*, 2005, vol. 61, pp. 60-68.

Labadie, et al., "In vitro assessment of image-guided otologic surgery: Submillimeter accuracy within the region of the temporal bone," *Otolaryngology-Head and Neck Surgery*, 2005, vol. 132(3), pp. 435-442.

Lobregt, S., et al., "Dental implant surgery: planning and guidance," *Medicamundi*, 2001, vol. 45(4), pp. 30-35.

Meyer, U., et al., "Evaluation of accuracy of insertion of dental implants and prosthetic treatment by computer-aided navigation in minipigs," *British Journal of Oral and Maxillofacial Surgery*, 2003, vol. 41, pp. 102-108.

NG, FC, e al., "Computer-assisted Navigational Surgery Enhances Safety in Dental Implantology," *Annals Academy of Medicine*, 2005, vol. 34(5), pp. 383-388.

Sieβegger, M. et al., "Use of an image-guided navigation system in dental implant surgery in anatomically complex operation sites," *Journal of Cranio-Maxillofacial Surgery*, 2001, vol. 29, pp. 276-281.

Widmann, G., et al., "Image-guided surgery and medical robotics in the cranial area," *Biomedical Imaging and Intervention Journal*, vol. 3(1):e11, pp. 1-9.

\* cited by examiner

GUIDED DENTAL IMPLANTATION SYSTEM AND ASSOCIATED DEVICE AND METHOD

CROSS-REFERENCE TO RELATED APPLICATION

This application claims the benefit of the filing date of U.S. Provisional Patent Application Ser. No. 61/041,722, filed Apr. 2, 2008, which is incorporated by reference herein in its entirety.

BACKGROUND OF THE INVENTION

1. Field of the Invention

Embodiments of the present invention are directed toward robotic systems for dental surgery and, more particularly, to a guided dental implantation system and associated device and method.

2. Description of Related Art

Patients who are missing teeth, whether it be one, several, or an entire arch, may be candidates for dental implants. Patients who want a more permanent solution than dentures, bridges, or other tooth replacement measures may also be interested in dental implants.

The dental implantation procedure generally involves an invasive incision into the gum of the patient in order to allow the practitioner to view the underlying jawbone structure. A hole is then drilled into the jawbone structure, into which a dental implant is placed (see, e.g., FIG. 1A). In some instances, the dental implant may be shaped, for example, like a screw. Once the dental implant is inserted into the jawbone structure, an external post is attached to the dental implant (see, e.g., FIG. 1B), and a prosthetic cap (tooth reproduction) attached to the post (see, e.g., FIG. 1C).

With computerized tomography (CT) and other imaging scans becoming more common, the practitioner may be able to graphically visualize the jawbone structure, without or before the invasive incision. However, the alignment of the dental implant with respect to the jawbone structure and/or relative to other implants or teeth may be an important factor in determining, for example, the life of the dental implant, the appearance thereof, and the comfort to the patient. If the dental implant is poorly or otherwise not optimally placed, the dental implant can undesirably fail (or at least have a shorter service life), may undesirably cause other teeth or dental implants to be compromised, and/or damage proximal nerves.

Thus, there exists a need for a system and method for providing an improved dental implantation procedure that addresses the noted shortcomings of current procedures, and facilitates, for example, effective pre-surgical planning and guidance during the surgical procedure.

BRIEF SUMMARY OF THE INVENTION

The above and other needs are met by the present invention which, in one aspect, provides a dental implantation system, comprising an implantation device adapted to prepare a site within a mouth of a patient for receiving a dental implant. A guidance device is operably engaged with the implantation device and is adapted to operably engage the mouth of the patient. The engagement between the guidance device and the mouth of the patient provides a fiducial marker for guiding the implantation device to prepare the site for receiving the dental implant.

Another aspect of the present invention provides a method of implanting a dental implant, comprising determining a fiducial marker from an engagement between a guidance device and a mouth of a patient; and guiding an implantation device operably engaged with the guidance device, with respect to the fiducial marker, so as to prepare a site within the mouth of the patient for receiving the dental implant.

Various other aspects of the present invention are directed to component devices and associated methods facilitating the dental implantation system and method of implanting a dental implant, as otherwise disclosed herein.

Aspects of the present invention thus provide distinct advantages as otherwise detailed herein.

BRIEF DESCRIPTION OF THE SEVERAL VIEWS OF THE DRAWING(S)

Figure 1B:
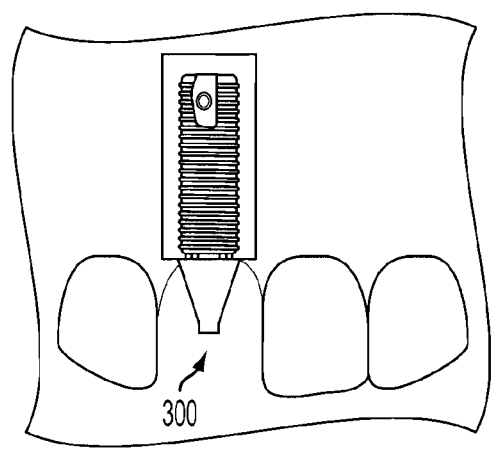
Figure 1C:
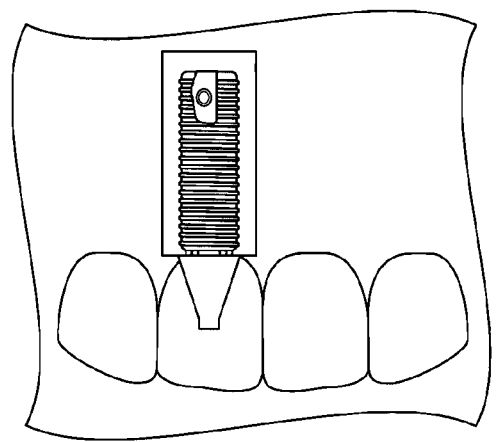
Figure 2:
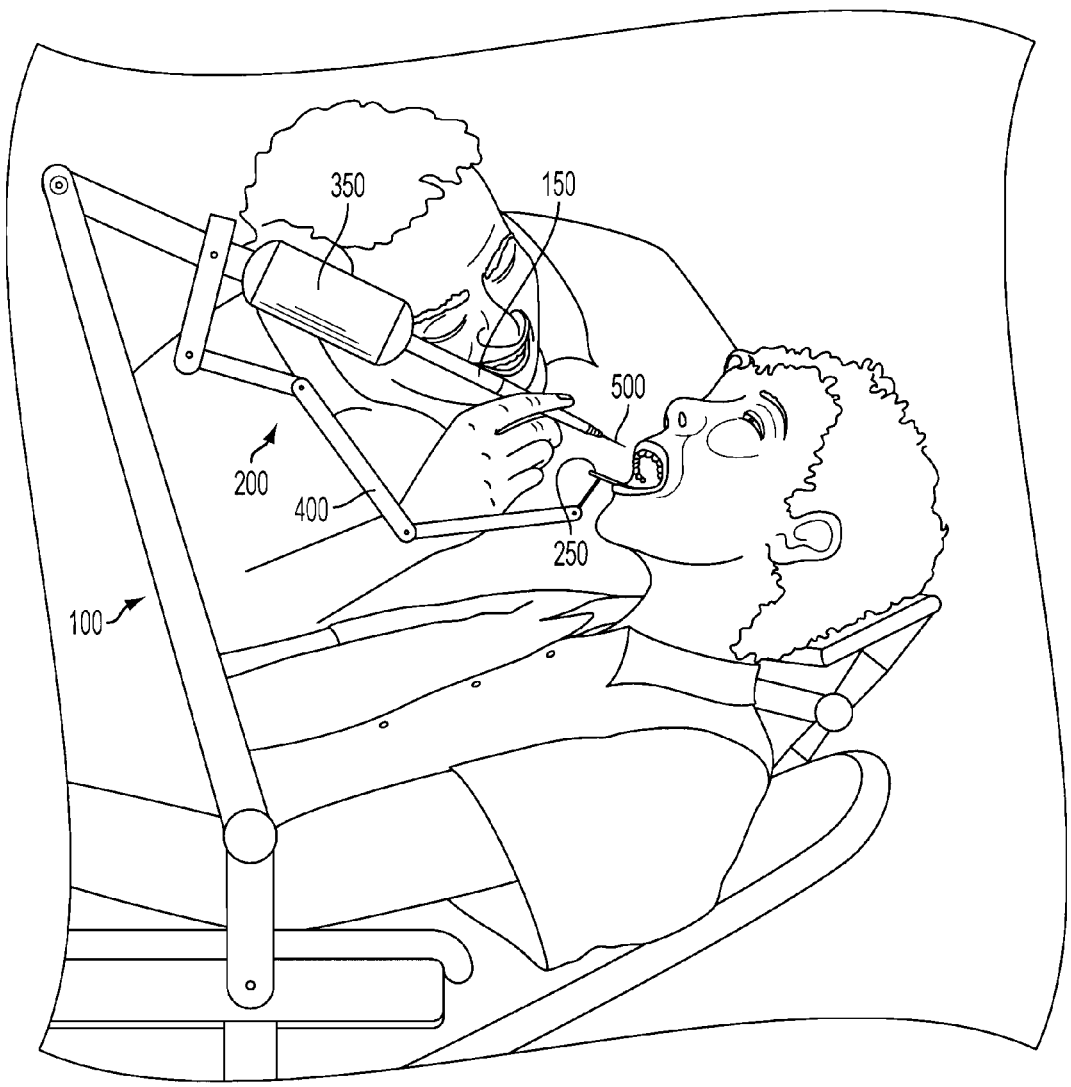
Figure 3:
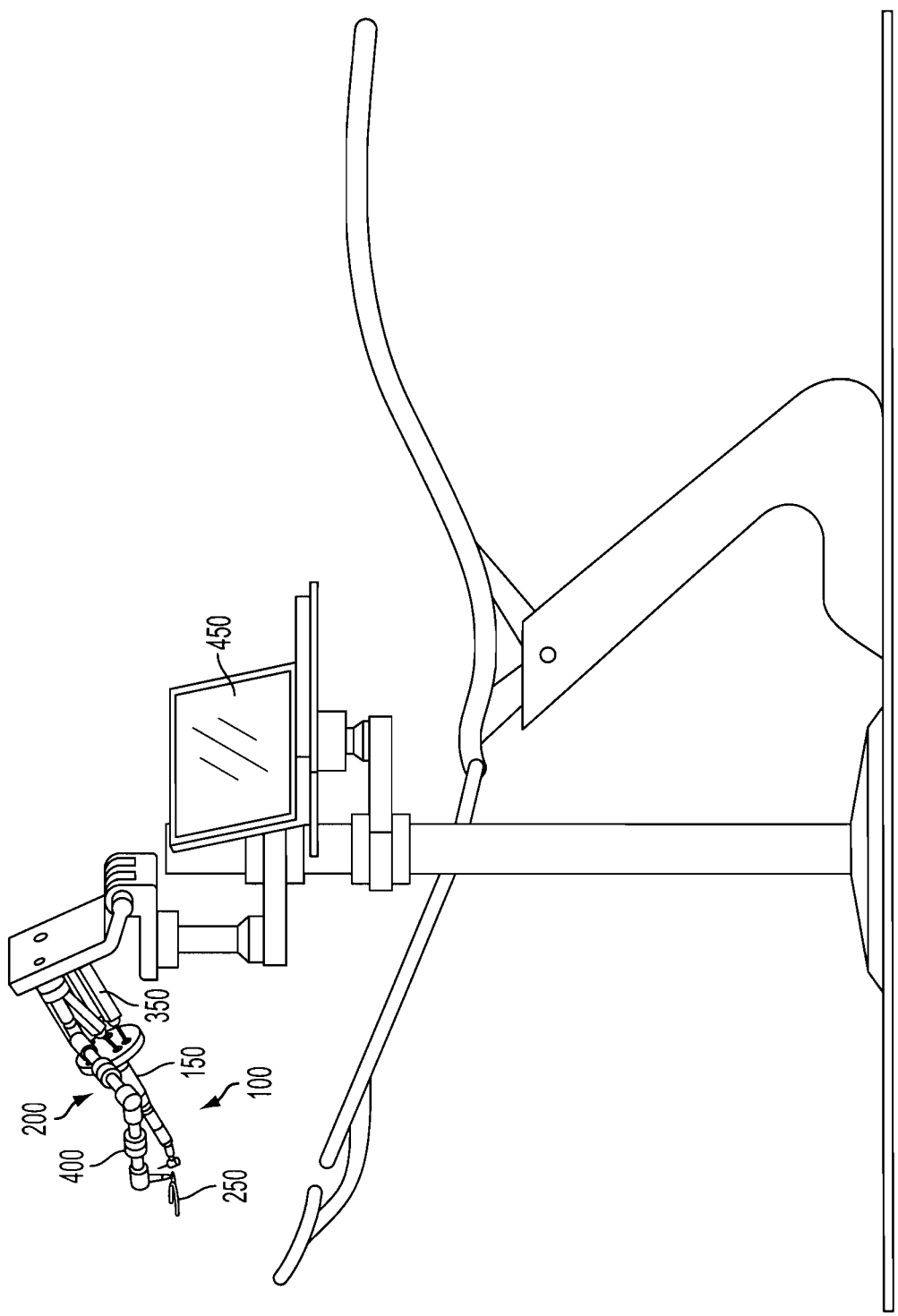
Figure 4:
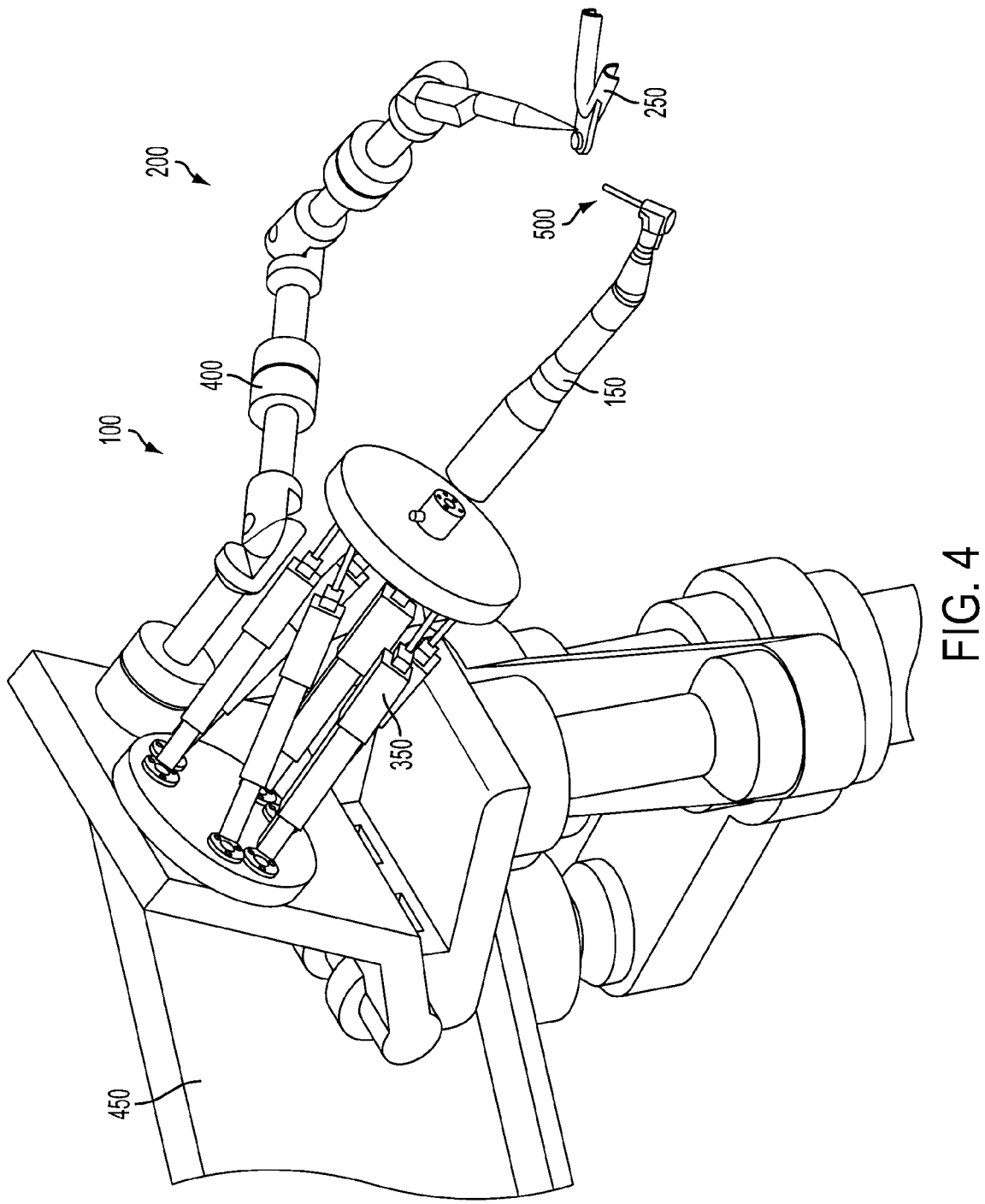
Figure 5:
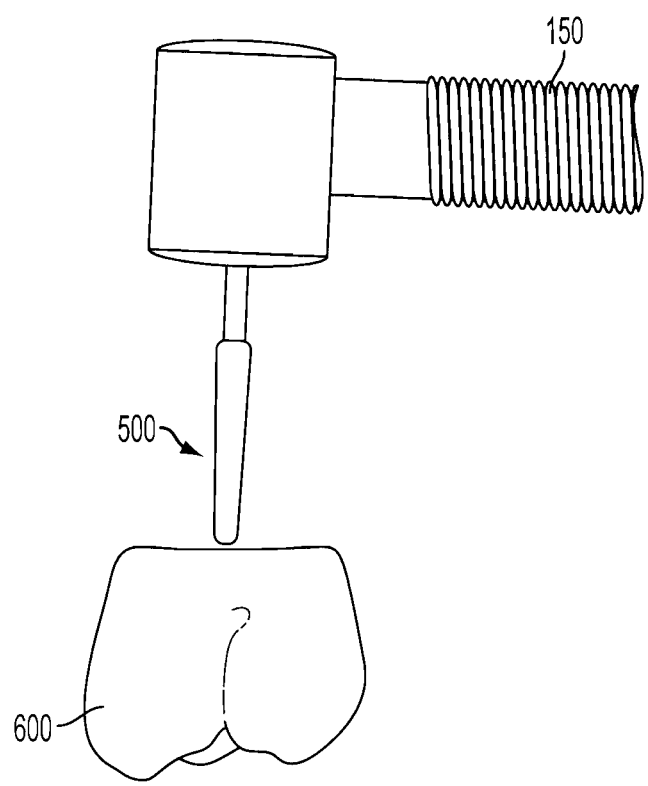

Having thus described the invention in general terms, reference will now be made to the accompanying drawings, which are not necessarily drawn to scale, and wherein:

FIGS. 1A-1C schematically illustrate a dental implantation procedure with respect to the mouth of a patient;

FIG. 2 schematically illustrates a dental implantation system according to one embodiment of the present invention;

FIGS. 3 and 4 schematically illustrate a dental implantation system according to an alternate embodiment of the present invention; and FIG. 5 schematically illustrates preparation of a prosthetic member with a dental implantation system according to one embodiment of the present invention.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

FIG. 2 and FIGS. 3 and 4 illustrate alternate embodiments of a dental implantation system according to the present invention, the system being generally indicated by the numeral 100. As previously indicated, current dental implantation procedures generally involve an imaging step, wherein CT or other appropriate images of the patient's jaw structure are obtained, and any anomalies diagnosed (i.e., whether the patient requires bone grafts to prepare the implant area). The practitioner then corrects any anomalies and proceeds with the invasive implant procedure based on the conditions associated with the patient's jaw structure, once the appropriate incisions have been made in the patient's gum.

A dental implantation system 100 according to various aspects of the present invention addresses the subjective aspects of current dental implantation procedures by providing a guided implantation device 150 (otherwise referred to herein as a "cutting device") configured to be guided with respect to the invasive portion of the dental implant procedure (i.e., to "prepare" the site within the patient's mouth). That is, the implantation device 150 is operably engaged with a guidance device 200. The guidance device 200 is adapted to operably engage the mouth of the patient. For example, the engagement with the mouth of the patient may be through a splint 250 or other engaging member. In one instance, the splint 250 is configured to engage the patient's mouth in a "firm" or secure interaction (i.e., the splint 250 is engaged with the patient's teeth and does not move with respect to the patient's mouth). Since the splint 250 does not move with respect to the patient's mouth, the disposition of the splint 250 is known, and thus can be configured to provide a fiducial marker (i.e., a known origin or coordinate) which can be used, for instance, to guide the implantation device to prepare the site in the patient's mouth for receiving the dental implant 300 (see, e.g., FIG. 1B). In one aspect, the splint 250 is configured to be "universally applicable" (i.e., capable of forming the secure engagement with the mouth of any patient), or at least applicable across a particular range of patients (i.e., one size fits a certain size or age of patient). In order to determine the fiducial marker, according to one aspect of the invention, the splint 250 may be engaged with the patient's teeth and the patient's jawbone structure then imaged using, for example, CT or any other suitable imaging technique such as, for instance, MRI.

With respect to the imaging procedure, one skilled in the art will appreciate that the implantation procedure generally involves only one jawbone structure. That is, the implant is generally intended to be placed in either the upper jawbone structure or the lower jawbone structure of the patient. As such, it may be important to obtain as clear and detailed an image of the subject jawbone structure as possible, which may be hindered by interference of the teeth of the opposing jawbone structure. Accordingly, it may be desirable to define a separation or other distinction between the upper and lower jawbone structures during the imaging procedure. Accordingly, the imaging procedure according to one embodiment of the present invention may further comprise a separator device (not shown) inserted between the patient's jawbone structures as the images are acquired. For example, such a separator device may comprise a block, plate, or other appropriate physical structure inserted into the patient's mouth, in conjunction with, or separate and discrete with respect to, the splint 250. The separator device may also include a separation indicator (not shown) element comprising a radiopaque material (i.e., a metallic material) that can be clearly defined in the image, wherein the separation indicator is disposed within or otherwise associated with the separator device so as to define a jawbone structure separation line, plane, or other suitable boundary. Accordingly, the separator device allows each jawbone structure to be imaged separately of the other (i.e., without interference) and, once the image is acquired, image processing techniques may be applied to the image in order to separate the image along the jawbone structure separation line, plane, or other boundary defined by the separation indicator so as to segregate (from the imaging standpoint) the jawbone structure receiving the implant. One skilled in the art will also appreciate that, since the configuration of the separation indicator is known, deviation from the configuration in the captured image may indicate, for example, undesirable movement of the patient during the imaging procedure. For example, a curved separation line shown in the image, when the separation indicator is actually a straight rod, may indicate that the patient moved during the imaging procedure, and that the procedure must be repeated to obtain a suitable image.

One skilled in the art will also appreciate that the splint 250 may be configured in many different manners to accomplish the desired function as discussed herein. For example, the splint 250 may be rigidly attached to the patient's mouth in an appropriate manner depending on the condition of the patient. That is, if the patient has some strong teeth capable of supporting the splint 250, the splint 250 can be attached to the teeth with an adhesive or with a suitable clamp. For edentulous patients (i.e., without teeth), bone pins may be drilled through the splint 250 and into the patient's jawbone structure to fasten the splint 250 securely into place. The splint 250 may also be attached to the jawbone structure of any patient using, for example, appropriate bone screws. In one aspect, the positioning of the splint 250 with respect to the patient's mouth may not be critical or important, as long as the splint 250 remains rigidly in place. A fiducial marker (not shown) may then be attached to, or otherwise incorporated into, the splint 250, wherein the fiducial marker may be configured to have a geometry or other characteristic or feature that uniquely defines the fiducial marker in a three-dimensional space (i.e., such that the fiducial marker is readily identified in images of the patient's jawbone structure). In such instances, the fiducial marker may be comprised of, for example, a radiopaque material that can be clearly defined in the image (e.g., CT or MRI).

In one instance, the implantation device 150 is engaged with an articulating arm member 350 (i.e., a robotic arm) which determines a range of motion of the implantation device 150. The guidance device 200, in such instances, may further comprise a communication element 400 in communication between the splint 250 and the implantation device 150 and/or the arm member 350. For example, the communication element 400 may comprise a mechanical linkage connecting the splint 250 to the implantation device 150/arm member 350. That is, the communication element 400 may comprise, for example, a mechanically-tracked arm which attaches to the splint 250 engaged with the patient. In some instances, the arm may be attached to the splint 250 (rigidly and in a known, repeatable manner) with an attachment mechanism comprising a kinematic mount. Attached to the patient in this manner via the attachment mechanism and the splint 250, the communication element 400 provides data (whether constantly, selectively, or otherwise as necessary) about the position of the patient (i.e., with respect to the fiduciary) to the implantation device 150/arm member 350, while still providing for accurate guidance thereof in the event that the patient moves. However, one skilled in the art will appreciate that the splint 250 and/or the fiducial marker determined thereby may be communicated to the implantation device 150/arm member 350 in many different manners. For example, the fiducial marker may be communicated via a communication element 400 comprising a wireless transceiver, a hardwire connection, an optical communication system, or any other suitable mechanism, whether electrical, mechanical, electromechanical, or optical in nature. In any instance, the guidance device 200 may be further configured to include a controller device 450 (i.e., a computer device as shown in FIGS. 3 and 4) for determining the fiducial marker from the image of the patient's mouth having the splint 250 disposed therein, and for appropriately communicating the fiducial marker to the implantation device 150/arm member 350.

In one aspect, the controller device 450 may be further configured to receive the image of the patient's jawbone structure (having the splint 250 therein). In some instances, the controller device 450 may be further configured to be capable of executing an implantation routine that may comprise software, hardware, or a combination thereof. The implantation routine thus allows the practitioner to create, for example, a virtual implantation plan based on the captured image, whether in two dimensions or three dimensions, and to manipulate the image(s) of the patient's jawbone structure in conjunction with a "virtual implant" in order to develop the virtual implantation plan or placement determination for the patient in conjunction with a computerized model based on the image(s). In some aspects, the implantation routine, virtual implantation plan, and/or placement determination may be created in relation, for example, to a coordinate system (relative or absolute), as will be appreciated by one skilled in the art, for associating the implantation parameters with the fiducial marker. In other aspects, the controller device 450 may include a peripheral device (i.e., a trackball or joystick in conjunction with, for example, 3 D goggles, all not shown) to assist with or otherwise permit virtual manipulation or placement of the virtual implant(s) with respect to the image(s) in order to, for example, align the implant(s) relative to each other or relative to adjacent teeth, to align the implant(s) relative to the affected nerve, and to align the implant(s) relative to the jawbone structure. The controller device 450 may be further configured to perform such manipulation manually, automatically, or semi-automatically, as necessary or desired. Because the virtual implant(s) may be manipulated in a similar manner to the image(s), the orientation or placement of the virtual implant(s) may represent the desired actual placement of the implant with respect to the patient's jawbone structure, thus providing an intuitive interface for planning the implantation procedure.

In aspects where the splint 250/fiducial marker approach is used, the patient is automatically registered with the system 100 once the communication element 400 (arm) is attached to the splint 250 via the kinematic mount of the attachment mechanism. That is, the fiducial marker is automatically determined from the image(s) of the patient's jawbone structure, and the alignment and location thereof in physical space is known due to the kinematic mount connecting the arm to the splint 250. One skilled in the art will appreciate, however, that other alignment approaches may be implemented that do not necessarily require a fiducial marker. For example, in some instances, a surface matching technique can be implemented. More particularly, the patient's jawbone structure may be manipulated into a 3 D configuration in the captured image(s). A suitable scanning device (i.e., a physical pointer or other imaging device such as an ultrasound transducer or OCT (optical coherence tomography) scanner may be attached to the end effector of the arm member 350 such that the tip of the arm member 350 is capable of scanning the patient's jawbone structure to "surface match" the captured and manipulated image(s) with an actual scan of the jawbone structure.

One skilled in the art will further appreciate that the association of the fiducial marker with the patient's anatomy, via the controller device 450, may be accomplished in different manners. For example, with respect to the registration of the image (e.g., CT scan) to the fiducial marker, one method could involve the jaw structure of the patient being imaged with the fiducial marker in place, as previously discussed, wherein the patient would then be substantially immediately subjected to the implantation procedure. Such a scheme may be beneficial, for example, in reducing the number of visits to the practitioner by the patient. However, in some instances, the practitioner may not have the imaging capabilities at hand, or may prefer to carefully determine the virtual implantation plan before carrying out the implantation procedure. In both such instances, the patient will likely be required to return to the practitioner at a later time. Accordingly, in such situations, a pre-operative imaging procedure (e.g., CT scan) may be performed on the jaw structure of the patient, without a fiducial marker in place (i.e., a "normal" scan by which the practitioner can determine the virtual implantation plan). This pre-operative imaging procedure can thus be performed, for example, at the practitioner's site, or at a dedicated scanning/imaging center. Subsequently, immediately prior to the implantation procedure being performed, and with the fiducial marker(s) engaged with the jaw structure of the patient, the practitioner may capture another image (e.g., CT scan, panoramic x-ray, or two single x-rays) of the patient's jaw structure. The controller device 450 may thus also be configured to correlate the pre-operative image (used to determine the virtual implantation procedure) with the "day of" image so as to register the fiducial marker(s) with respect to the original pre-operative image. Such a registration or correlation procedure may be implemented in hardware, software, or a combination thereof, as will be appreciated by one skilled in the art. The implantation procedure could then proceed as otherwise disclosed herein.

In any instance, the communication element 400 is configured to engage the arm member 350 in a manner known to the system 100, such that the position/movement characteristics of the end effector are also known. This communication between the communication element 400 and the arm member 350 thus allows the implantation device 150 to be registered with respect to the fiducial marker (or other reference with respect to the patient) attached to the patient via the splint 250, the kinematic mount, the communication element 400, and the arm member 350. In this manner, the virtual implantation process, planned through the controller device 450, may be accomplished in relation to the fiducial marker (or other reference with respect to the patient) and thus translated or otherwise communicated to the system 100 for directing the implantation device 150.

The implantation device 150 is disposed in or otherwise engaged with the end effector of the arm member 350 (robotic arm). The arm member 350 may be configured, for example, to provide six degrees of freedom and can also be configured to restrict or otherwise control the movement of the implantation device 150. Further, the arm member 350 may have a miniature parallel structure to which the implantation device 150 is secured and allowed to have full freedom of movement when not in cutting/preparation/implantation mode. Since the implantation device 150 is attached to the end effector of the arm member 350, the patient interacting portion (i.e., the cutting/drilling tip) 500 (see, e.g., FIGS. 2 and 4) of the implantation device 150 must be in a known position (i.e., known to the system 100) relative to the arm member 350. In some aspects, in order to calibrate the interacting portion 500 of the implantation device 150 with respect to the fiducial marker, a calibration element may be engaged with the implantation device 150 via a kinematic coupling (i.e., rigidly mounted thereto in a known, repeatable manner). One skilled in the art will thus appreciate that the interacting portion 500 of the implantation device 150 can then be calibrated with various tip calibrating methods (i.e., invariant point, etc.). Once calibrated, the calibration element is replaced with a cutting/drilling element in the implantation device 150, in a known and repeatable manner, so that the calibration parameters (i.e., the position of the distal-most point and axis of cutting/drilling) associated with the interacting portion 500 are maintained as calibrated.

With the alignment with respect to the patient established and known by the system 100, and the virtual implantation plan developed through the controller device 450, the implantation procedure (i.e., cutting/drilling/insertion) can then be initiated by the practitioner moving the implantation device 150 toward the patient's mouth (having the splint 250 engaged therewith). In such instances, the controller device 450 is configured to control the movement of the implantation device 150 via the arm member 350 such that the action of the practitioner merely moves interacting portion 500 (i.e., the cutting/drilling element) to the appropriate starting position for the implantation procedure, with respect to the patient's jawbone structure, as determined by the controller device 450 and dictated by the virtual implantation plan. Once the cutting/drilling element is in the position dictated by the controller device 450, the invasive portion of the procedure can then be initiated, wherein the controller device 450 may further dictate other parameters of the implantation device 150 such as, for example, the orientation of the path of the cutting/drilling element and the cutting/drilling distance along that path from the cutting/drilling origin, also according to the virtual implantation plan. In these instances, one distinction of the system 100 disclosed herein is that the implantation device 150 is not guided by the practitioner, but is only urged by the practitioner along a procedural route determined via the virtual implantation plan and implemented via the controller device 450 and the arm member 350. That is, the system 100 may be configured to restrict the practitioner to performing the implantation procedure with respect to the patient, as determined via the virtual implantation plan and implemented via the controller device 450 and the arm member 350, whereby the controller device 450 controls the allowable movement of the arm member 350 (and thus the implantation device 150) in accordance with the virtual implantation plan created from the image(s) of the patient's jawbone structure. For instance, the system 100 may be configured for restricted movement of the arm member 350/implantation device 150, as communicated to the practitioner through tactile feedback, where, for example, the arm member 350/implantation device 150 may be easier to move according to the virtual implantation plan, and more difficult to move if deviating from the virtual implantation plan. One skilled in the art will also appreciate, however, that the physical structure of the arm member 350/implantation device 150 to provide fully controlled movement according to the virtual implantation plan (i.e., due to vibration, flexing of components, and/or excessive force applied by the practitioner) and, as such, the system 100 may be further configured to provide other manners of feedback to the practitioner such as, for example, via a deviation warning indicia or any other suitable audio and/or visual mechanism. Therefore, the system 100 includes provisions for actually implementing the virtual implantation plan, and thus facilitates a more accurate implantation procedure, rather than merely warning the practitioner if any procedural parameters may be inaccurate. One skilled in the art will also appreciate, however, that, in some instances, the system 100 may be further configured to autonomously accomplish the virtual implantation plan, without the manipulation of the practitioner, through automatic manipulation of the arm member 350/implantation device 150 via the controller device 450.

In one exemplary surgical procedure using a dental implantation system 100, as disclosed herein, the splint 250 (i.e., mouthpiece) is first attached to the patient's teeth, and thus provides a fiducial marker. The patient's jawbone structure is then imaged (with the splint 250 in place and engaged with the patient's teeth) using, for example, CT or any other appropriate imaging technique (e.g., MRI), and the image(s) communicated with the controller device 450. The controller device 450 may be further configured to be capable of executing an implantation routine, thus allowing the practitioner to develop an implantation plan for the patient, for example, by manipulating a virtual implant with respect to the captured image(s). Once the virtual implantation plan is created, the communication element 400 is engaged with the splint 250 (attached to the patient's mouth, with the patient being positioned in a suitable position to initiate the procedure). The arm member 350, implantation device 150, and interacting portion 500 thereof, are then calibrated by the practitioner (or automatically by the controller device 450), before the actual cutting/drilling element of the implantation device 150 is used by the practitioner (or autonomously via the controller device 450), via the implantation device 150 as guided by the arm member 350 and the controller device 450, to accomplish the implantation procedure as planned and dictated by the virtual implantation plan.

According to other aspects of the present disclosure, a prosthetic member 600 (e.g., a denture, reproduction tooth, etc.) may be prepared or otherwise modified by the dental implantation system 100 to complementarily engage the dental implant previously implanted by the implantation system 100, by facilitating an aligned engagement therebetween. That is, the dental implantation system 100 may be configured to prepare the prosthetic member(s) 600 in a manner that allows the prosthetic member 600 to precisely correspond to and engage the dental implant, as planned and dictated by the virtual implantation plan, so that correct alignment therebetween is achieved when the prosthetic member 600 is permanently placed with respect to the dental implant within the patient's mouth. In one example, the interacting portion 500 (e.g., drill element) of the implantation device 150 may be configured to and controlled by the controller device 450 to remove material from the prosthetic member 600 to form a borehole which is complementary to and configured to receive a corresponding portion of the dental implant, as shown in FIG. 5. For example, in one instance, the dental implant may extend beyond the jawbone/gum line of the patient so as to provide a post or projecting member upon which the prosthetic member 600 may be mounted, seated, or otherwise secured within the patient's mouth. Thus, the borehole of the prosthetic member 600 may be particularly formed by the dental implantation system 100 to facilitate alignment of the prosthetic member 600 with the dental implant.

In order to form the borehole in the appropriate location or site of the prosthetic member 600, the prosthetic member 600 may be registered with the implantation routine (i.e., registered with respect to the fiducial marker associated with the splint 250). In one instance, the prosthetic member 600 may be introduced within the virtual implantation plan and "virtually" registered with the system 100 in relation to the fiducial marker associated with the splint 250. In other instances, the prosthetic member 600 may be appropriately positioned within the patient's mouth at the time of the initial scan of the patient's jawbone structure, as previously described, so as to be physically registered with the fiducial marker associated with the splint 250. In such instances, the prosthetic member 600 may also have one or more fiducial markers (e.g., metallic bearing members) attached to, incorporated in, or otherwise associated therewith, wherein the prosthetic member fiducial marker(s) may be configured to have a particular geometry or other unique characteristic or feature that readily identifies and defines those fiducial marker(s) in the images of the patient's jawbone structure, as well as in comparison to the fiducial marker associated with the splint 250. As disclosed, the fiducial marker(s) associated with the prosthetic member 600 may be comprised of, for example, a radiopaque material that can be clearly defined in the image (e.g., CT or MRI). By implementing the prosthetic member fiducial marker(s), the configuration of the prosthetic member 600 with respect those fiducial marker(s) can be determined, and thus the system 100 can be configured and guided according to the prosthetic member fiducial marker(s) (i.e., according to a coordinate system associated with the prosthetic member 600 and registered with the system 100) so as to allow the implantation device 150 to prepare the borehole at the appropriate site in the prosthetic member 600.

As a result of the imaging (and/or virtual implantation plan), the prosthetic member fiducial marker(s) may be identified in the imaging scans and then related to/registered with the system 100 so as to allow the borehole to be appropriately formed in the prosthetic member 600. That is, once the prosthetic member 600 is registered with or known to the controller device 450, the interacting portion 500 (or a calibration member), whether coupled to the implantation arm 150/arm member 350 or not, may be brought into engagement with the fiducial member(s) associated with the physical prosthetic member 600, with the prosthetic member 600 fastened or otherwise held in a static position, to associate the physical prosthetic device 600 with the system such that the borehole can be formed therein according to the virtual implantation plan. In any instance, the capability of preparing the prosthetic member 600 via the system 100 provides an expedited dental implantation process by facilitating a more accurate alignment between the dental implant and prosthetic member 600.

Many modifications and other embodiments of the inventions set forth herein will come to mind to one skilled in the art to which these inventions pertain having the benefit of the teachings presented in the foregoing descriptions and the associated drawings. For example, one skilled in the art will appreciate that the systems, devices, and methods disclosed herein may also be applicable to other surgical procedures such as, for instance, in neurosurgery operations involving the formation of a bore in the cranium. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A dental implantation system, comprising:
    an implantation device adapted to prepare a site within a mouth of a patient for receiving a dental implant; and
    a guidance device physically engaged with the implantation device, the guidance device being adapted to securely and physically interact with the mouth of the patient, the secure and physical interaction between the guidance device and the mouth of the patient forming a fiducial marker, the implantation device thereby being configured to be in physical communication with the fiducial marker, and the guidance device being further configured to physically regulate movement of the implantation device with respect to the fiducial marker, in accordance with a virtual implantation plan and in correspondence with physical manipulation of the implantation device by a user, to prepare the site for receiving the dental implant, at least one of the guidance device and the implantation device being configured to provide tactile feedback to the user if the physical manipulation of the implantation device by the user deviates from the virtual implantation plan.

2. A system according to claim 1 further comprising a splint device adapted to securely and physically interact with the mouth of the patient to form the fiducial marker, the splint device being in physical communication with the guidance device and cooperable therewith to physically relate the guidance device to the fiducial marker.

3. A system according to claim 1 further comprising an arm member physically engaged with the implantation device and the guidance device, the arm member being responsive to the guidance device to guide the physical manipulation of the implantation device by the user according to the virtual implantation plan to prepare the site for receiving the dental implant.

4. A system according to claim 1 further comprising a dental implant planning system configured to facilitate graphical manipulation of a jawbone structural image of the patient for forming the virtual implantation plan of the site within the mouth of the patient for receiving the dental implant.

5. A system according to claim 4 wherein the dental implant planning system is further configured to be in communication with at least the guidance device for translating the virtual implantation plan to the implantation device.

6. A method of implanting a dental implant, comprising:
    forming a fiducial marker through a secure and physical interaction between a guidance device and a site within a mouth of a patient; and
    physically regulating movement of an implantation device with the guidance device and with respect to the fiducial marker, the implantation device being physically engaged with the guidance device and thereby being in physical communication with the fiducial marker, the movement of the implantation device being physically regulated, in accordance with a virtual implantation plan and in correspondence with physical manipulation of the implantation device by a user, to prepare the site for receiving the dental implant; and
    providing tactile feedback to the user, via at least one of the guidance device and the implantation device, if the physical manipulation of the implantation device by the user deviates from the virtual implantation plan.

7. A method according to claim 6 further comprising engaging the mouth of the patient with a splint device in physical communication with the guidance device, the splint device being adapted to securely and physically interact with the mouth of the patient to form the fiducial marker, and being cooperable therewith to physically relate the guidance device to the fiducial marker.

8. A method according to claim 6 wherein physically regulating movement of the implantation device further comprises physically regulating movement of the implantation device with an arm member physically engaged with the implantation device and the guidance device, the arm member being responsive to the guidance device to guide the physical manipulation of the implantation device by the user according to the virtual implantation plan.

9. A method according to claim 6 further comprising forming the virtual implantation plan of the site within the mouth of the patient for receiving the dental implant with a dental implant planning system configured to facilitate graphical manipulation of a jawbone structural image of the patient.

10. A method according to claim 9 wherein the dental implant planning system is further configured to be in communication with at least the guidance device, and the method further comprises translating the virtual implantation plan from the dental implant planning system to the implantation device.

11. A method according to claim 6 further comprising implanting the dental implant at the site prepared by the implantation device.

12. A method according to claim 11 further comprising relating a prosthetic member with one of the fiducial marker and the guidance device, and guiding the physical manipulation of the implantation device by the user with the guidance device according to the virtual implantation plan to prepare the prosthetic member for aligned engagement with the dental implant implanted at the site.

13. A method according to claim 12 wherein relating a prosthetic member with the guidance device further comprises:

engaging at least one prosthetic member fiducial marker with the prosthetic member; and registering the at least one prosthetic member fiducial marker with the guidance device.

14. A method according to claim 12 wherein relating a prosthetic member with one of the fiducial marker and the guidance device further comprises incorporating the prosthetic member into the virtual implantation plan of the site within the mouth of the patient, with respect to the dental implant, with the dental implant planning system, and translating the virtual implantation plan including the prosthetic member from the dental implant planning system to the implantation device.

15. A method according to claim 12 wherein the dental implant comprises a projecting member and preparing the prosthetic device further comprises forming a channel in the prosthetic device with the implantation device, the physical manipulation thereof by the user being guided by the guidance device, the channel being complementarily configured with respect to the projecting member according to the virtual implantation plan, so as to provide an aligned engagement therebetween upon the projecting member being received by the channel.

\* \* \* \* \*